United States Patent [19]

Durette et al.

[11] Patent Number: 4,760,161
[45] Date of Patent: Jul. 26, 1988

[54] IPOXYGENASE INHIBITORS

[75] Inventors: Philippe L. Durette, New Providence; Timothy F. Gallagher, Metuchen, both of N.J.

[73] Assignee: Merck & Co., Inc., Rahway, N.J.

[21] Appl. No.: 488,498

[22] Filed: Apr. 25, 1983

[51] Int. Cl.$^4$ .............................................. C07C 69/76
[52] U.S. Cl. ..................... 560/008; 560/20; 560/64; 564/163; 564/170; 564/171; 568/731; 568/659
[58] Field of Search ............... 560/8, 20, 64; 564/163, 564/170, 171; 168/731, 659; 574/132, 534, 538, 717

[56] References Cited

U.S. PATENT DOCUMENTS 3,896,143  7/1975  Kathawala ..................... 548/379

FOREIGN PATENT DOCUMENTS 2644789  4/1977  Fed. Rep. of Germany .
2383157  10/1978  France .
46-06651  4/1971  Japan ..................... 560/008

OTHER PUBLICATIONS

Meyer et al. CA81(17)1053732, 1974.
Walsh R. et al., CA88(19):131385u, 1977.
Yamato M. et al., CA87(3):17711b, 1977.
Tashchuk K. et al., CA79(15):91692x, 1973.
Karanewsky, R., CA 104(17)148549x, (1985).

Shidhar, D. R. Indian J. Chem Sect. B 20B(5) 401-3, 1981.
Japanese Patent Specification J57,106,651 as shown in Derwent Farmdoc No. 66912E/32.
D. Bailey et al., Ann Rpts. Med. Chem., 17 203-217 (1982).
R. C. Murphy et al., PNAS USA 76 4275 (1979).
J. L. Humes et al., J. Biol. Chem., 257 1591 (1982).
H. R. Morris et al., Prostaglandins, 19 371 (1980).
M. E. Vol'pin et al., Zh. Obsh. Khim., 29 2855 (1959).
T. Asao et al., Chem. Lett., (1978) 41.

Primary Examiner—Paul J. Killos
Attorney, Agent, or Firm—Donald J. Perrella; Hesna J. Pfeiffer

[57] ABSTRACT

Compounds of the Formula I:

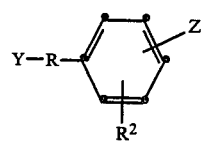

and pharmaceutically acceptable salts thereof are inhibitors of leukotriene biosynthesis. These compounds inhibit lipoxygenase, thus preventing the metabolism of arachidonic acid to the leukotrienes. These compounds are thus useful in the treatment of asthma, allergic disorders, inflammation, skin diseases and certain cardiovascular disorders.

9 Claims, No Drawings

IPOXYGENASE INHIBITORS

BACKGROUND OF THE INVENTION

This invention is directed to new chemical compounds, especially useful as inhibitors of lipoxygenase enzyme systems. Lipoxygenase controls the biosynthesis of the class of compounds known as leukotrienes. Inhibition of lipoxygenase therefore prevents or diminshes the adverse effects of the leukotrienes in a human subject.

The leukotrienes are a novel group of biologically active mediators derived from arachidonic acid through the action of lipoxygenase enzyme systems. The leukotrienes play an important role in inducing allergic reactions, such as asthma, allergic bronchitis or allergic rhinitis in man. One of the leukotrienes ($B_4$) contributes to both inflammation and allergic reactions in man.

There are two groups of leukotrienes derived from the common unstable precursor Leukotriene $A_4$. The first of these are the peptido-lipid leukotrienes, the most important Leukotrienes $C_4$ and $D_4$. These compounds collectively account for the biological activity known as slow reacting substances of anaphylaxis. They are potent smooth muscle contracting agents, particularly on respiratory smooth muscle but also on other tissues (e.g., gall bladder). In addition, they promote mucous production, modulate vascular permeability changes and are potent inflammatory agents in human skin.

The most important compound in the second group of leukotrienes is leukotriene $B_4$, a dihydroxy fatty acid derived from leukotriene $A_4$. This compound is a potent chemotactic agent for neutrophils ad eosinophils. When injected in vivo, in addition to promoting the accumulation of leukocytes, leukotriene $B_4$ is also a potent hyperalgesic agent and can modulate vascular permeability changes through a neutrophil dependent mechanism. Both groups of leukotrienes are formed following oxygenation of arachidonic acid through the action of 5-lipoxygenase enzyme. See D. Bailey and F. Casey, *Ann. Rpts. Med. Chem.* 17 203 (1982).

Leukotrienes can also mediate other diseases. These include psoriasis, atopic dermatitis, gouty arthritis and gall bladder spasms. In addition, they may have a role in cardiovascular disease because leukotrienes $C_4$ and $D_4$ act as coronary and cerebral arterial vasoconstrictors and these compounds may also have negative ionotropic effects on the myocardium. In addition, leukotrienes are important mediators of inflammatory diseases through their ability to modulate leukocyte and lymphocyte function.

SUMMARY OF THE INVENTION

This invention is directed to novel compounds of the Formula I:

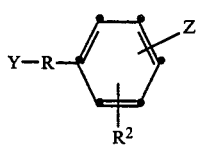

and pharmaceutically acceptable salts thereof wherein the various substituents are as defined herein below.

This invention provides novel compounds that act as inhibitors of lipoxygenase, thus preventing the synthesis of the leukotrienes $C_4$, $D_4$ and $E_4$ and also leukotriene $B_4$.

This invention also provides a method of treatment for disease states caused by the synthesis of the leukotrienes $C_4$, $D_4$, $E_4$ and $F_4$, as well as leukotriene $B_4$, in a human subject. This method comprises administering to said subject an effective amount of a compound of Formula I combined with an appropriate pharmaceutical carrier.

DETAILED DESCRIPTION OF THE INVENTION

This invention is directed to novel compounds of the Formula I:

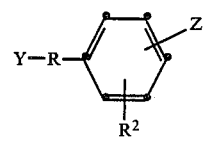

wherein
Y is

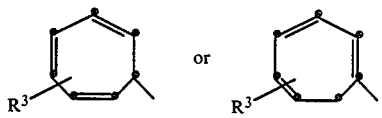

Z is

R is

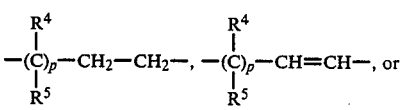

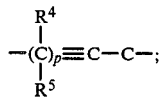

$R^1$ is hydrogen, loweralkyl;
$R^2$, $R^3$, $R^4$ and $R^5$ are each independently: hydrogen, halogen, loweralkyl, alkyl, hydroxy, loweralkoxy, amino, monoloweralkyl substituted amino, diloweralkyl substituted amino, benzyl, benzyl substituted with one or more $R^6$, aralkyl, aralkyl substituted with one or more $R^6$, phenyl, phenyl substituted with one or more $R^6$;
$R^6$ is alkyl, halogen, hydroxy, loweralkoxy, amino, nitro, trihaloalkyl;
$R^7$ is $C_1$-$C_7$ loweralkyl;
$R^8$, $R^9$ and $R^{10}$ are independently hydrogen or $C_1$-$C_6$-loweralkyl;
m is an integer of from 1–6;
n is an integer of from 0–5;
p is an integer of from 0–4,
and pharmaceutically acceptable salts thereof.

SCHEME I

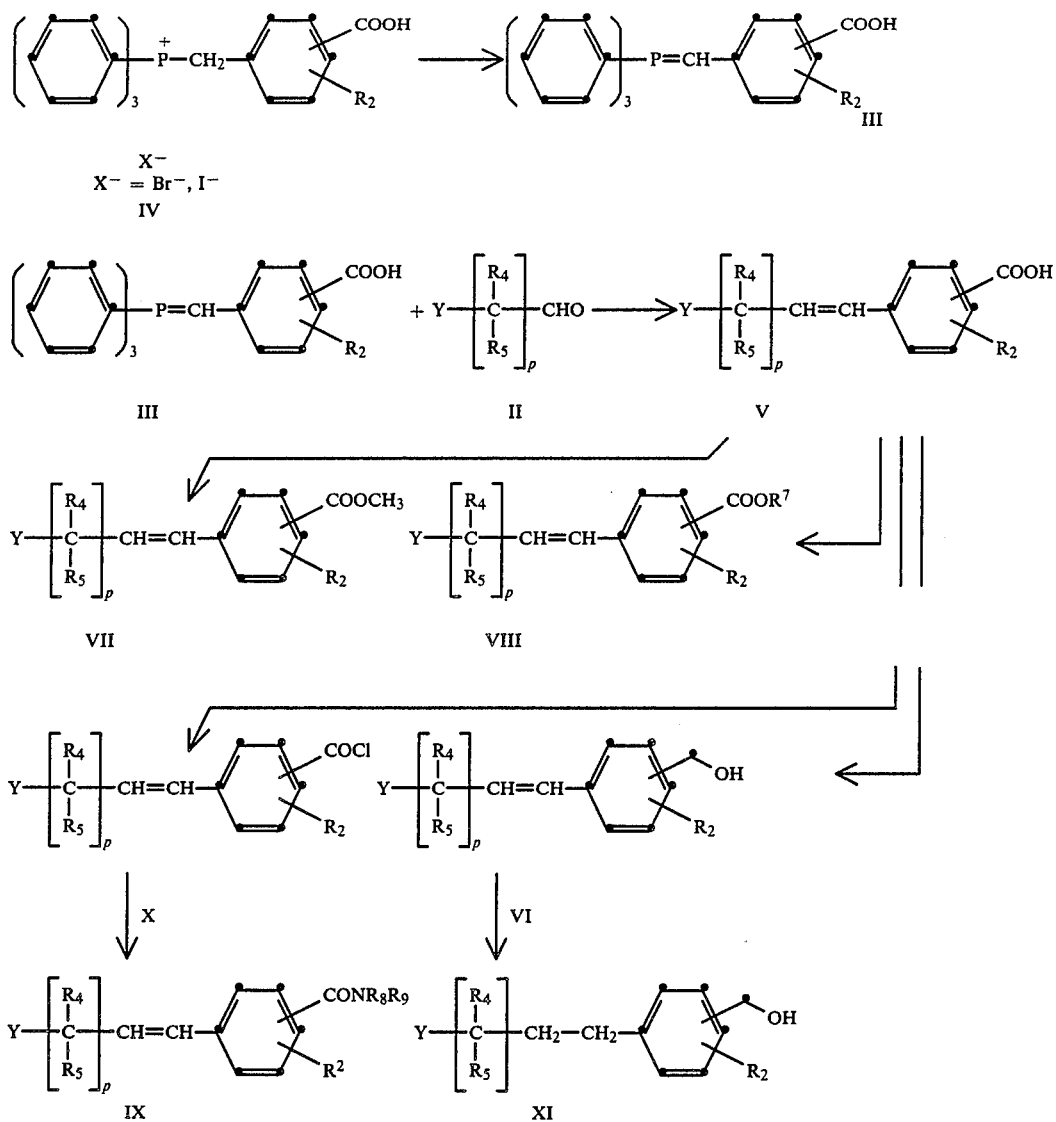

As used herein, loweralkyl is defined as a straight or branched, and where appropriate, cyclic or acyclic, saturated or unsaturated group containing from 1 to 8 carbon atoms, unless otherwise specified. The term alkyl is intended to represent such groups having from 1 to 20 carbon atoms. The term halogen includes fluorine, bromine, chlorine and iodine. The term aryl includes the aromatic groups, naphthalene, phenanthrene, anthracene, and the like.

As illustrated in Scheme I, the compounds of the present invention are prepared by reaction of the appropriate aldehyde (II) with the appropriate phosphorane (III) derived by treatment of the appropriate substituted-benzyl triphenylphosphonium halide (IV) (preferably, bromide or iodide) in a solvent, such as diethyl ether, tetrahydrofuran, dimethyl sulfoxide, or alcohol, with a strong base (e.g., an organolithium compound, such as n-butyllithium or phenyllithium; sodium hydride; or sodium amide) or a moderately strong base, such as a metal alkoxide (e.g., sodium ethoxide or potassium tert-butoxide). The Wittig reaction is performed at a temperature of from $-25°$ C. to $100°$ C. for from 30 min. to 24 hr. The starting aldehyde is either known or can be made by known procedures.

Conversion of the alkenylbenzoic acids (V) into the alkenylbenzyl alcohols (VI) is achieved by metal hydride reduction, i.e., treatment of the acid with a metal hydride, such as lithium borohydride, sodium borohydride, lithium aluminum hydride, diborane, or the like, in a solvent, such as diethyl ether, tetrahydrofuran, dimethoxyethane, diglyme, p-dioxane, ethanol, ethanol, isopropanol, or the like, at a temperature of from $0°$ to $85°$ C. for from 30 minutes to 24 hours.

The acids (V) are converted into their methyl ester (VII) derivatives either by (a) treatment with diazomethane in a solvent such as diethyl ether, dichloromethane, tetrahydrofuran, or the like at a temperature of from $-10°$ to $25°$ C. for from 5 minutes to 1 hour; or (b) treatment with methanol in the presence of an acid catalyst such as hydrogen chloride, concentrated sulfuric acid, or acidic ion-exchange resin, in particular, with an exchange resin containing sulfonic acid groups, e.g., Amberlite IR-120 (resins of styrene containing strongly acidic sulfonyl groups) or Dowex-50 (polystyrene sulfonic acids) at reflux temperature for from 12 to 48 hours; or (c) treatment of an alkali salt, such as sodium salt, with a methylating agent, such as iodomethane, in a solvent such as N,N-dimethylformamide, hexamethylphosphoric triamide, or the like, at room temperature for from 15 minutes to 24 hours.

The $C_2$-$C_7$ ester derivatives (VIII) are prepared by treatment of an alkali salt of the acid (V) such as a potassium or sodium salt, with an alkylating agent, such as iodoalkane or bromoalkane, in a suitable solvent such as N,N-dimethylformamide or hexamethylphosphoric triamide, or the like, at room temperature for from 15 minutes to 24 hours.

The acids (V) may be converted into their amide derivatives (IX) by first converting them into the acid chloride, by treatment with a chlorinating agent such as thionyl chloride, oxalyl chloride, or the like, in a solvent such as diethyl ether, dichloromethane, tetrahydrofuran, or the like, at a temperature of from $-25°$ to $25°$ from from 5 minutes to several hours. The acid chloride (X) may then be reacted with the appropriate primary or secondary amine in a solvent such as dichloromethane, tetrahydrofuran, or the like, optionally in the presence of an acid acceptor, such as pyridine, triethylamine, 4-dimethylaminopyridine, and the like, at a temperature of from $-25°$ to $25°$ for from 5 minutes to 24 hours.

The alkenylbenzyl alcohols (VI) are converted into alkylbenzyl alcohols (XI) by treatment in a solvent, such as methanol, ethanol, ethyl acetate, or the like, in the presence of a catalyst, such as palladium-on-charcoal, rhodium-on-carbon, palladium-on-barium sulfate, or the like, under a hydrogen pressure of from 1 to 5 atmospheres, at a temperature of from $20°$ to $50°$ C.

them to the alkenylbenzoic acids (V) by treatment with aqueous alkali hydroxide, such as sodium or potassium hydroxide in a solvent, such as methanol, ethanol, or the like, at a temperature of from $50°$ to $100°$ C. for from 12 to 73 hours. The acids are then reduced to the alcohols (VI) as described above.

The Formula I compounds are potent inhibitors of the 5-lipoxygenase pathway of arachidonic acid metabolism and have little or no inhibiting effect on the cyclooxygenase pathway of arachidonic acid metabolism.

The compounds of Formula I are active as inhibitors of the biosynthesis of both leukotriene $B_4$, as well as leukotrienes $C_4$, $D_4$, $E_4$ and $F_4$, the active elements of slow reacting substance of anaphylaxis (SRS-A). This inhibition of the biosynthesis of leukotrienes indicates that the compositions are useful to treat, prevent or ameliorate, in mammals and especially in humans, pulmonary conditions including diseases such as asthma; and allergies and allergic reactions such as allergic rhinitis, contact dermatitis, and allergic conjunctivitis. These compounds are also useful as anti-inflammatory and analgesic agents; and in the treatment of skin diseases, such as psoriasis; and in the treatment of cardiovascular conditions, such as angina.

Inhibition of leukotriene synthesis by the compounds of Formula I was determined by their ability to (a) inhibit rat basophilic leukemia (RBL-1) 5-lipoxygenase; (b) inhibit synthesis and/or release of leukotriene-$C_4$ in vitro from mouse peritoneal macrophages; (c) inhibit leukotriene-$B_4$ synthesis and/or release from rat peritoneal polymorphonuclear leukocytes; and (d) inhibit ovalbumin-induced contractions of sensitized smooth muscle strips. These assays are known to the skilled artisan. See for example; (a) R. C. Murphy et al., *PNAS USA*, 76, 4275 (1979; (b) J. L. Humes et al., *J. Biol. Chem.*, 257, 1591 (1982); (c) E. A. Ham et al., *PNAS*

SCHEME II

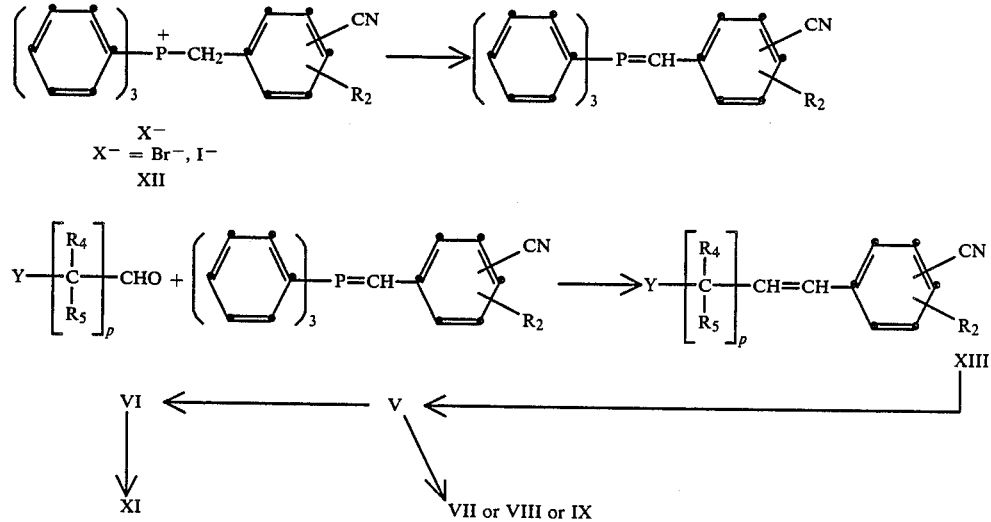

In the case where a carboxybenzyltriphenylphosphonium salt is employed in the Wittig reaction, as illustrated in Scheme I, a carboxyphenylalkene (III) is obtained. In the case where a cyanobenzyl triphenylphosphonium salt (XII) is used, as illustrated in Scheme II, a cyanophenylalkene (XIII) is obtained.

The cyanophenylalkenes (XIII) are converted into the alkenylbenzyl alcohols (VI) by first hydrolyzing

*USA*, in press (1983); and (d) H. R. Morris et al., *Prostaglandins*, 19, 371 (1980).

The magnitude of a prophylactic or therapeutic dose of a compound of Formula I will, of course, vary with the nature of the severity of the condition to be treated and with the particular compound of Formula I and its route of administration. In general, the daily dose range lies within the range of from about 10 μg to about 50 mg, preferably from about 1 mg to about 20 mg, per kg body weight of a mammal.

The pharmaceutical compositions of the present invention comprise a compound of formula I as an active ingredient, and may also contain a pharmaceutically acceptable carrier and optionally other therapeutic ingredients. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well known in the art of pharmacy.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount. These inhalation formulations will range in dosage from about 0.1 μg to about 200 μg of a compound of Formula I, administered as necessary to provide relief.

Pharmaceutical compositions of the present invention suitable for oral administration and by inhalation in the case of asthma therapy may be presented as discrete units such as capsules, cachets or tablets each containing a predetermined amount of the active ingredient, as a powder or granules, or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent.

The following examples illustrate the present invention without, however, limiting the same thereto. Temperatures are expressed in °C. and are uncorrected.

EXAMPLE 1

1-[4'-(Hydroxymethyl)-phenyl]-3-(1',3',5'-cycloheptatrien-7'-yl)-trans-1-butene

Step A:
1-(4'-Carboxyphenyl)-3-(1',3',5'-cycloheptatrien-7'-yl)-trans-1-butene

A mixture of 1.29 g (26.9 mmol) of 50% sodium hydride in mineral oil and 30 ml of dimethyl sulfoxide was stirred under nitrogen for 1.5 hours at 75°. The resulting mixture was cooled to ambient temperature, and a solution of (4-carboxybenzyl)triphenylphosphonium bromide (6.44 g, 13.49 mmol) in dimethyl sulfoxide (20 ml) was added. The resulting dark red solution was stirred under nitrogen for 1 hour at room temperature. To this mixture was added dropwise with stirring a solution of α-cycloheptatrienylpropionaldehyde [prepared by the process set forth in M. E. Vol'pin et al., Zh. Obsh. Khim., 29, 2855 (1959)] (1.0 g, 6.75 mmol) in dimethyl sulfoxide (10 ml). After 30 minutes, the reaction was quenched by addition to a mixture of 0.2M sodium bisulfate in ice-water and diethyl ether. The aqueous layer was extracted with ether, and the combined organic extracts were washed with water, dried (sodium sulfate), and evaporated. The crude product was chromatographed on a column of silica gel (E. Merck No. 7734, packed as a slurry in 1:8 ether-hexane). Elution with 1:8 ether-hexane containing 1% acetic acid afforded a white solid that was recrystallized from ether-hexane; yield 808 mg (45%), m.p. 137°-140°. The 300 MHz NMR spectrum in chloroform-d indicated trans (E) geometric isomer.

Anal. Calc. for $C_{18}H_{18}O_2$: C, 81.17; H, 6.81. Found: C, 81.14; H, 6.86.

Step B:
1-[4'-(Hydroxymethyl)-phenyl]-3-(1',3',5'-cycloheptatrien-7'-yl)-trans-1-butene To a solution of 1-(4'-carboxyphenyl)-3-(1',3',5'-cycloheptatrien-7'-yl)-trans-1-butene (200 mg, 0.75 mmol) in tetrahydrofuran (15 ml) was added lithium aluminum hydride (57 mg). The reaction mixture was stirred under nitrogen for 1 hour at room temperature and quenched by the sequential addition of water (57 μl), 15% aqueous sodium hydroxide (57 μl), and water (171 μl). The mixture was filtered through Celite, the filter washed with tetrahydrofuran, and the combined filtrate and washings evaporated. The residue was taken up in diethyl ether, washed with water, and dried (sodium sulfate). Pure 1-[4'-(hydroxymethyl)-phenyl]-3-(1',3',5'-cycloheptatrien-7'-yl)-trans-1-butene was obtained as a colorless syrup by chromatography on silica gel (E. Merck No. 7734; elution with 1:3 ether-hexane); yield 156 mg (82%); mass spectrum m/z 252 (M).

The 200 MHz NMR spectrum in chloroform-d was in accord with the desired structure (trans stereochemistry).

EXAMPLE 2

1-[4'-(Methoxycarbonyl)-phenyl]-3-(1',3',5'-cycloheptatrien-7'-yl)-trans-1-butene The title compound was obtained in quantitative yield by treatment of 1-(4'-carboxyphenyl)-3-(1',3',5'-cycloheptatrien-7'-yl)-trans-1-butene in cold dichloromethane with diazomethane. The 200 MHz NMR spectrum of the product in chloroform-d was in accord with the desired structure: δ 3.68 (s, 3H, COOC$H_3$)

EXAMPLE 3

1-[4'-(Hydroxymethyl)-phenyl]-3-(1',3',5'-cycloheptatrien-7'-yl)-trans-1-propene Employing the procedure substantially as described in Example 1, but substituting for the α-cycloheptatrienylpropionaldehyde used in Step A thereof, an equivalent amount of cycloheptatrienylacetaldehyde

[prepared by the process set forth in M. E. Vol'pin et al., *Z. Obsh. Khim.*, 29, 2855 (1959)], there were prepared in sequence:

Step A:
1-(4'-Carboxyphenyl)-3-(1',3',5'-cycloheptatrien-7'-yl)-trans-1-propene

Mass spectrum: m/z 252 (M). The 200 MHz NMR spectrum in chloroform-d was in accord with the desired structure, indicating trans (E) stereo-chemistry.

Step B:
1-[4'-Hydroxymethyl)-phenyl]-3-(1',3',5'-cycloheptatrien-7'-yl)-trans-1-propene Mass spectrum: m/z 238 (M). The 300 MHz NMR spectrum in chloroform-d was in accord with the desired structure, indicating trans (E) stereo-chemistry.

EXAMPLE 4

1-[4'-(Hydroxymethyl)-phenyl]-3-(1',3',5'-cycloheptatrien-7'-yl)-3-methyl-trans-1-Butene Employing the procedure substantially as described in Example 1, but substituting for the α-cycloheptatrienylpropionaldehyde used in Step A thereof, an equivalent amount of α-cycloheptatrienylisobutyraldehyde [prepared by the process set forth in M. E. Vol'pin et al., *Z. Obsh. Khim.*, 29, 2855 (1959)], there are prepared in sequence:

Step A:
1-(4'Carboxyphenyl)-3-(1',3',5'-cycloheptatrien-7'-yl)-3-methyl-trans-1-butene The 200 MHz NMR spectrum is in accord with the desired structure (trans stereochemistry).

Step B:
1-[(4'-Hydroxymethyl)-phenyl]-3-(1',3',5'-cycloheptatrien-7'-yl)-3-methyl-trans-1-butene The 200 MHz NMR spectrum is in accord with the desired structure (trans stereochemistry).

EXAMPLE 5

1-[4'-(Dimethylaminocarbonyl)-phenyl]-3-(1',3',5'-cycloheptatrien-7'-yl)-trans-1-butene To a solutio of 1-[4'-(hydroxymethyl)-phenyl]-3-(1',3',5'-cycloheptatrien-7'-yl)-trans-1-butene (75 mg, 0.28 mmol) in dichloromethane (10 ml) were added triethylamine (78 μl) and thionyl chloride (21 μl). The reaction mixture was stirred for 1 hour at room temperature and evaporated. The residue was taken up in tetrahydrofuran (5 ml), and the mixture was added to a solution of 40% aqueous dimethylamine (200 μl) and triethylamine (78 μl) in tetrahydrofuran (10 mL). After 15 minutes, the reaction mixture was evaporated, the residue taken up in diethylether, washed with 2N hydrochloric acid, saturated aqueous sodium hydrogencarbonate, saturated aqueous sodium chloride, and evaporated. Pure dimethylamide was obtained by chromatography on a column of silica gel (E. Merck No. 7734; elution with 2:1 ether-hexane); yield 61 mg (74%).

The 60 MHz NMR spectrum in chloroform-d was in accord with the desired structure [δ2.98 (s, 6H, CON-Me$_2$)].

EXAMPLE 6

1-[3'-(Hydroxymethyl)-phenyl]-3-(1',3',5'-cycloheptatrien-7'-yl)-1-butene

Step A:
1-(3'-Cyanophenyl)-3-(1',3',5'-cycloheptatrien-7'-yl)-1-butene

A mixture of 323 mg (6.73 mmol) of 50% sodium hydride in mineral oil and 8 ml of dimethyl sulfoxide was stirred under nitrogen for 1.5 hours at 75°. The resulting mixturewas cooled to ambient temperature, and a solution of (3-cyanobenzyl)triphenylphosphonium bromide (3.09 g, 6.74 mmol) in dimethyl sulfoxide (10 ml) was added. The resulting red solution was stirred under nitrogen for 1 hour at room temperature. To this solution was added dropwise with stirring a solution of α-cycloheptatrienylpropionaldehyde (500 mg, 3.37 mmol) in dimethyl sulfoxide (8 ml). After 30 minutes, the reaction was quenched by pouring into a mixture of water and diethyl ether. The aqueous layer was extracted with ether, and the combined organic extracts were washed with water, dried (sodium sulfate), and evaporated. The residue was dissolved in a small volume of dichloromethane, and the solution was applied to a column of silica gel (E. Merck No. 7734; packed as a slurry in 1:20 ether-hexane). Elution with 1:20 ether-hexane yielded pure nitrile; yield 334 mg (40%).

Step B:
1-(3'-Carboxyphenyl)-3-(1',3',5'-cycloheptatrien-7'yl)-1-butene

A solution of 1-(3'-cyanophenyl)-3-(1',3',5'-cycloheptatrien-7'-yl)-1-butene (180 mg, 0.73 mmol) in ethanol (8 ml) was treated with 10% aqueous potassium hydroxide (3 ml). The mixture was stirred for 1 day at 90°, cooled, and evaporated. The residue was diluted with water and the mixture brought to pH∼2 with 2N hydrochloric acid. The product was extracted with diethyl ether (2×), and the combined extracts washed with saturated aqueous sodium chloride, dried (sodium sulfate), and evaporated. The product was purified by chromatography on silica gel (E. Merck No. 7734; packed as a slurry in 1:8 ether-hexane; elution with 1:8 ether-hexane containing 1% acetic acid); yield 118 mg (61%).

Step C:
1-[3'-(Hydroxymethyl)-phenyl]-3'-(1',3',5'-cycloheptatrien-7'yl)-1-butene A solution of 1-(3'-carboxyphenyl)-3-(1',3',5'-cycloheptatrien-7'yl)-1-butene (115 mg, 0.43 mmol) in tetrahydrofuran (10 ml) was treated with lithium aluminum hydride (37 mg) under nitrogen for 1 hour at room temperature. Excess lithium aluminum hydride was decomposed by sequential addition of water (37 μl), 15% aqueous sodium hydroxide (37 μl), and water (111 μl). The mixture was filtered through Celite, the filter washed with tetrahydrofuran, and the combined filtrate and washings evaporated. The residue was taken up in ether, washed with water, and dried (sodium sulfate). The product was purified by thick layer argentation chromatography on plates (0.50 mm) of silica gel GF$_{254}$ (Analtech) with 5:1 ether-hexane as the developer and extraction with ether; yield 88 mg (81%).

The 300 MHz NMR spectrum in chloroform-d was in accord with the desired structure.

EXAMPLE 7

1-[4′-(Hydroxymethyl)-phenyl]-3-(1′,3′,5′-cycloheptatrien-7′-yl)-cis-1-butene

Step A:
1-(4′-Carboxyphenyl)-3-(1′,3′,5′-cycloheptatrien-7′-yl)-cis-1-butene The mother liquor from the crystallization of 1-(4′-carboxyphenyl)-3′-(1′,3′,5′-cycloheptatrien-7′-yl)-trans-1-butene (Example 1, Step A) was evaporated, and a second crop of the trans-isomer was obtained by crystallization from ether-hexane. Several repetitions of this process resulted in isolation of pure cis-isomer from the final mother liquor. The 300 MHz NMR spectrum in chloroform-d indicated cis-(Z) stereochemistry.

Step B:
1-[4′-(Hydroxymethyl)-phenyl]-3-(1′,3′,5′-cycloheptatrien-7′-yl)-cis-1-butene Treatment of 1-(4′-carboxyphenyl)-3-(1′,3′,5′-cycloheptatrien-7′-yl)-cis-1-butene with lithium aluminum hydride in tetrahydrofuran for 1 hour at room temperature and work-up of the reaction employing the procedure as described in Step B of Example 1 gave pure 1-[4′-(hydroxymethyl)-phenyl]-3-(1′,3′,5′-cycloheptatrien-7′-yl)-cis-1-butene.

EXAMPLE 8

1-[4′-(2″-Hydroxyethyl)-phenyl]-3-(1′,3′,5′-cycloheptatrien-7′-yl)-trans-1-butene

Step A:
1-[4′-(Chloromethyl)-phenyl]-3-(1′,3′,5′-cycloheptatrien-7′-yl)-trans-1-butene To a solution of 1-[4′-(hydroxymethyl)-phenyl]-3-(1′,3′,5′-cycloheptatrien-7′-yl)-trans-1-butene (Example 1) (334 mg, 1.32 mmol) and triphenylphosphine (694 mg, 2.65 mmol) in pyridine (9 ml) was added carbon tetrachloride (1.33 mL). The mixture was allowed to attain room temperature and, after stirring for 1 hour, was evaporated and coevaporated with toluene. Addition of ether to the residue gave a solid that was removed by filtration. The filtrate was evaporated, dissolved in a small volume of dichloromethane, and the solution applied to a column of silica gel (E. Merck No. 7734; packed as a slurry in hexane). Initial elution with hexane removed faster-moving impurities and subsequent elution with 1:10 ether-hexane gave pure chloride; yield 165 mg. (46%).

Step B:
1-[4′-(Cyanomethyl)-phenyl]-3-(1′,3′,5′-cycloheptatrien-7′-yl)-trans-1-butene A solution of 1-[4′-(chloromethyl)-phenyl]-3-(1′,3′,5′-cycloheptatrien-7′-yl)-trans-1-butene (165 mg, 0.61 mmol) in N,N-dimethylformamide (8 ml) was treated with sodium cyanide (64 mg, 1.3 mmol) for 1 hour at 60°. The mixture was evaporated, the residue partitioned between ether and water, the aqueous layer extracted with ether, the combined organic extracts evaporated and coevaporated with methanol. The product was purified by chromatography on silica gel (E. Merck No. 7734; elution with 1:8 ether-hexane); yield 120 mg (75%).

Step C:
1-[4′-(Carboxymethyl)-phenyl]-3-(1′,3′,5′-cycloheptatrien-7′-yl)-trans-1-butene 1-[4′-(Cyanomethyl)-phenyl]-3-(1′,3′,5′-cycloheptatrien-7′-yl)-trans-1-butene (120 mg, 0.46 mmol) in ethanol (5 ml) was hydrolyzed in the presence of 10% aqueous potassium hydroxide (1.5 ml) overnight at 80°. The cooled mixture was concentrated, the residue taken up in water, and brought to about pH 2 with 2N hydrochloric acid. The product was extracted with ether and purified by chromatography on silica gel (E. Merck No. 7734; packed as a slurry in 1:5 ether-hexane; elution with 1:5 ether-hexane containing 1% acetic acid; yield 83 mg (64%).

The 200 MHz NMR spectrum in chloroform-d indicated trans-stereochemistry; $\delta$3.62 (s, 2H, —C$\underline{H}$$_2$CO$_2$H).

Step D:
1-[4′-(2″-Hydroxyethyl)-phenyl]-3-(1′,3′,5′-cycloheptatrien-7′-yl)-trans-1-butene Treatment of 1-[4′-(carboxymethyl)-phenyl]-3-(1′,3′,5′-cycloheptatrien-7′-yl)-trans-1-butene (15.6 mg) with lithium aluminum hydride (5 mg) in tertrahydrofuran for 30 minutes at room temperature and workup employing the procedure as described in Step B of Example 1 afforded pure product after chromatography on silica gel (E. Merck No. 7734; elution with 1:3 ether-hexane).

The 200 MHz NMR spectrum in chloroform-d was in accord with the desired structure: $\delta$3.85 (t, 2H, —C$\underline{H}$$_2$OH), 2.86 (t, 2H, —C$\underline{H}_2$CH$_2$OH).

EXAMPLE 9

1-[4′-(Hydroxymethyl)-phenyl]-2-[4′-(n-octylphenyl)]-trans-ethene

Step A:
1-(4′-Carboxyphenyl)-2-[4′-(n-octylphenyl)]-trans-ethene

A mixture of 438 mg (9.12 mmol) of 50% sodium hydride in mineral oil and 10 ml of dimethyl sulfoxide was stirred under nitrogen for 1.5 hours at 75°. The resulting mixture was cooled to ambient temperature, and a solution of (4-carboxybenzyl)-triphenylphosphonium bromide (2.18 g, 4.56 mmol) in dimethyl sulfoxide (10 ml) was added. The resulting mixture was stirred under nitrogen for 1 hour at room temperature. To this mixture was added dropwise with stirring a solution of 4-n-octylbenzaldehyde (500 mg, 2.29 mmol) in dimethyl sulfoxide (5 ml). After 30 minutes, the reaction was quenched by addition to a mixture of 0.2M sodium bisulfate in ice-water and diethyl ether. The aqueous layer was extracted with ether, and the combined organic extracts were washed with water, dried (sodium sulfate), and evaporated. The crude product was purified by chromatography on a column of silica gel (E. Merck No. 7734, elution with ether-hexane mixture containing 1% acetic acid); yield 393 mg (51%); mass spectrum: m/z 336 (M).

The 200 MHz NMR spectrum in dimethyl sulfoxide-d$_6$ indicated trans (E) stereochemistry.

Step B:
1-[4'-(Hydroxymethyl)-phenyl]-2-[4'-(n-octylphenyl)]-trans-ethene

Reduction of 1-(4'-carboxyphenyl)-2-[4'-(n-octylphenyl)]-trans-ethene with lithium aluminum hydride in tetrahydrofuran afforded pure 1-[4'-(hydroxymethyl)-phenyl]-2-[4'-n-octylphenyl)]-trans-ethene after chromatography on a column of silica gel (E. Merck, No. 7734, elution with 1:3 ether-hexane); mass spectrum: m/z 322 (M); m.p. 153°–154.5°.

The 200 MHz NMR spectrum in chloroform-d was in accord with the desired structure.

EXAMPLE 10
1-[4'-(Hydroxymethyl)-phenyl]-2-(1',3',5'-cycloheptatrien-1'-yl)-trans-ethene

Step A:
1-(4'-Carboxyphenyl)-2-(1',3',5'-cycloheptatrien-1'-yl)-trans-ethene A mixture of sodium hydride (50% in mineral oil; 1.4 g, 15 mmol) and dimethyl sulfoxide (35 ml) was heated to 75° for 1.5 hours under a nitrogen atmosphere. The solution was cooled, and (4-carboxybenzyl)triphenylphosphonium bromide (7.3 g, 15 mmol) was added. The resulting red solution was stirred for 1 hour at ambient temperature. A solution of 1-(formyl)-cycloheptatriene [prepared by the process set forth in T. Asao et al., Chem. Lett. (1978) 41] (0.92 g, 7.7 mmol) in dimethyl sulfoxide (5 ml) was added dropwise over several minutes. After stirring for 0.5 hours at ambient temperature, the reaction mixture was partitioned between 0.2M sodium bisulfate and ether. The layers were separated, and the aqueous phase was extracted twice with ether. The combined ether extracts were washed with saturated aqueous sodium chloride, dried (sodium sulfate) and evaporated. The residue was triturated with dichloromethane, and the solid recrystallized from methanol to give pure 1-(4'-carboxyphenyl)-2-(1',3',5'-cycloheptatrien-1'-yl)-trans-ethene (7.6%) as yellow crystals; yield 14 mg (7.6%); m.p. 127°–130°; mass spectrum m/z 238 (M).

The 300 MHz NMR spectrum in dimethyl sulfoxide-d-6 indicated trans (E) geometry.

Step B:
1-[4'-Hydroxymethyl)-phenyl]-2-(1',3',5'-cycloheptatrien-1'-yl)-trans-ethene A solution of 1-(4'-carboxyphenyl)-2-(1',3',5'-cycloheptatrien-1-yl)-trans-ethene (0.30 g, 1.3 mmol) in tetrahydrofuran (10 ml) was added dropwise to a suspension of lithium aluminum hydride (50 mg 1.3 mmol) in tetrahydrofuran (10 ml). The mixture was stirred at ambient temperature for 3 hours. The reaction mixture was cooled, and excess lithium aluminum hydride was destroyed by the sequential addition of water (0.1 ml), 15% aqueous sodium hydroxide (0.1 ml) and water (0.3 ml). The precipitate was removed by filtration, and the filtrate evaporated. The residue was partitioned between water and ether. The organic layer was washed with saturated aqueous sodium chloride, dried (sodium sulfate) and evaporated. The residue was subjected to column chromatography on silica gel (E. Merck No. 7734). Elution with 2:1 hexane-ether afforded a yellow solid; yield 0.16 g (51%); m.p. 82°–84°; mass spectrum m/z 224 (M).

EXAMPLE 11
1-[4'-(Hydroxymethyl)-phenyl]-3-phenyl-trans-1-butene

Step A: 1-(4'-Carboxyphenyl)-3-phenyl-trans-1-butene

A mixture of sodium hydride (50% in mineral oil; 3.4 g, 70 mmol) and dimethyl sulfoxide (50 ml) was heated to 75° for 1.5 hours under a nitrogen atmosphere. The solution was cooled to ambient temperature, and (4-carboxybenzyl)triphenylphosphonium bromide (18 g, 37 mmol) was added. The resulting red solution was stirred for 1 hour at ambient temperature. A solution of α-phenylpropionaldehyde (2.5 g, 19 mmol) in dimethyl sulfoxide (10 ml) was added over a ten minute period. Stirring was continued for an additional twenty minutes. The reaction mixture was poured into 0.2M sodium bisulfate, and the resulting mixture was extracted three times with ether. The combined ether extracts were washed with saturated aqueous sodium chloride, dried (sodium sulfate) and evaporated. The residue was subjected to column chromatography on silica gel (E. Merck No. 7734). Elution with 1% acetic acid in 1:1 hexane-ether afforded pure 1-(4'-carboxyphenyl)-3-phenyl-trans-1-butene as a white solid; yield 48 mg (10%); m.p. 127°–130°; mass spectrum m/z 252 (M), 237 (M—CH$_3$).

The 300 MHz NMR spectrum in chloroform-d indicated trans-(E) geometry.

Step B:
1-[4'-(Hydroxymethyl)-phenyl]-3-phenyl-trans-1-butene

A solution of 1-(4'-carboxyphenyl)-3-phenyl-trans-1-butene (0.35 g, 1.5 mmol) in tetrahydrofuran (25 ml) was added dropwise to a suspension of lithium aluminum hydride (56 mg) in tetrahydrofuran. The reaction was refluxed for 3 hours and cooled to ambient temperature. Excess lithium aluminum hydride was decomposed by the sequential addition of water (0.1 ml), 15% aqueous sodium hydroxide (0.1 ml) and water (0.3 ml). The precipitate was removed by filtration and the filtrate evaporated. The residue was subjected to column chromatography on silica gel (E. Merck No. 7734). Elution with 3:1 hexane-ether afforded pure 1-[4'-(hydroxymethyl)-phenyl]-3-phenyl-trans-1-butene; yield 0.22 g (65%); mass spectrum m/z: 238 (M), 223 (M—CH$_3$).

EXAMPLE 12
1-[4'-(hydroxymethyl)-phenyl]-3-phenylbutane

Rhodium-on-carbon (10 mg) was added to a solution of 1-[4'-hydroxymethyl)-phenyl]-3-phenyl-trans-1-butene (60 mg, 0.25 mmol) in absolute ethanol (5 ml), and the mixture was stirred for 2 hours at ambient temperature under a stream of hydrogen. The reaction was filtered through a pad of Celite, and the catalyst washed with ethanol. The combined filtrate and washings were evaporated to afford a quantitative yield of 1-[4'-(hydroxymethyl)-phenyl]-3-phenylbutane; mass spectrum m/z: 240 (M).

What is claimed is :
1. Compounds having the formula:

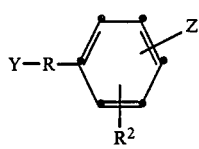

wherein

Y is

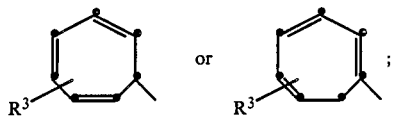

Z is

R is

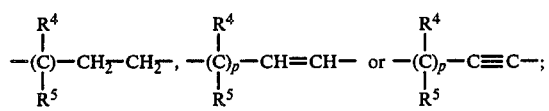

$R^1$ is hydrogen, loweralkyl;

$R^2$, $R^3$, $R^4$ and $R^5$ are each independently: hydrogen, halogen, loweralkyl, alkyl, hydroxy, loweralkoxy, amino, monoloweralkyl substituted amino, diloweralkyl substituted amino, benzyl, benzyl substituted with one or more $R^6$, aralkyl, aralkyl substituted with one or more $R^6$, phenyl, phenyl substituted with one or more $R^6$;

$R^6$ is alkyl, halogen, hydroxy, loweralkoxy, amino, nitro, trihalo alkyl;

$R^7$ is $C_1$–$C_7$loweralkyl;

$R^8$, $R^9$ and $R^{10}$ are each independently hydrogen or $C_1$–$C_6$loweralkyl;

m is an interger of from 1–6;

n is an interger of from 0–5;

p is an interger of from 0–4;

and pharmaceutically acceptable salts thereof.

2. The compounds of claim 1 wherein R is:

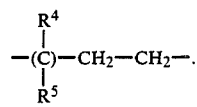

3. The compounds of claim 1 wherein R is

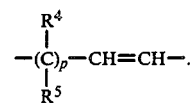

4. The compounds of claim 1 wherein R is:

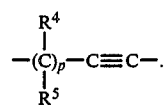

5. The compounds of claim 1:
1-[4'-(hydroxymethyl9-phenyl]-3-(1',3',5'-cycloheptatrien-7'-yl)-trans-1-butene;
1-[4'-(methoxycarbonyl)-phenyl]-3-(1',3',5'-cycloheptatrien-7'-yl)-trans-butene;
1-[4'-(hydroxymethyl)-phenyl]-3-(1',3',5'-cycloheptatrien-7'-yl)-trans-1-propene;
1-[4'-(hydroxymethyl)-phenyl]-3-(1',3',5'-cycloheptatrien-7'-yl)-3-methyl-trans-1-butene;
1-[4'-(dimethylaminocarbonyl)-phenyl]-3-(1',3',5'-cycloheptatrien-7'-yl)-trans-1-butene;
1-[3'-(hydroxymethyl)-phenyl]-3-(1',3',5'-cycloheptatrien-7'-yl)-1-butene;
1-[4'-(hydroxymethyl)-phenyl]-3-(1',3',5'-cycloheptatrien-7'-yl)-cis-1-butene;
1-[4'-(2''-hydroxyethyl)-phenyl]-3-(1',3',5'-cycloheptatrien-7'-yl)-trans-1-butene;
1-[4'-(hydroxymethyl)-phenyl]-2-(1',3',5'-cycloheptatrien-1'-yl)-trans-ethene.

6. A composition containing a compound of claim 1 and a pharmaceutical carrier.

7. A method of inhibiting the actions of lipoxygenase in mammals, especially humans, which comprises administering to said mammals a pharmaceutically effective amount of the composition of claim 6.

8. A method of treating asthma, allergic disorder, inflammation, skin diseases and certain cardiovascular disorders in humans which comprises administering to said humans a pharmaceutically effective amount of the composition of claim 6.

9. A compound of claim 1 wherein Z is

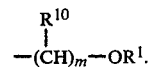

* * * * *